United States Patent [19]

Eskeland et al.

[11] Patent Number: 5,641,517
[45] Date of Patent: Jun. 24, 1997

[54] COMPOSITION COMPRISING FERTILIZED SHELL EGGS

[75] Inventors: Bjødne Eskeland, Ås; Peder Gjendemsjø, Nesoddtangen, both of Norway

[73] Assignee: Drymed AS, Oslo, Norway

[21] Appl. No.: 211,954
[22] PCT Filed: Jul. 22, 1993
[86] PCT No.: PCT/GB93/01553
    § 371 Date: Jan. 20, 1995
    § 102(e) Date: Jan. 20, 1995
[87] PCT Pub. No.: WO94/03192
    PCT Pub. Date: Feb. 17, 1994

[30] Foreign Application Priority Data

Jul. 29, 1992 [NO] Norway ............................... 922988
Jul. 8, 1993 [GB] United Kingdom .................. 9314335

[51] Int. Cl.⁶ .................................................. A61K 35/54
[52] U.S. Cl. .................................................. 424/520
[58] Field of Search .................................... 424/520

[56] References Cited

FOREIGN PATENT DOCUMENTS 1059230 2/1967 United Kingdom.

OTHER PUBLICATIONS

Chemical Abs vol. 84 No. 7 41005h (16 Feb. 1976) Woods et al.
Reynolds et al "Martindale the Extra Pharmacopedia" 1989 the Pharmaceutical Press, London GB pp.1383–1384 (3874x).

*Primary Examiner*—Herbert J. Lilling
*Attorney, Agent, or Firm*—Testa, Hurwitz & Thibeault, LLP

[57] ABSTRACT

Fertilized incubated shell eggs, e.g. avian eggs and in particular hens eggs, may be used to produce a composition which acts to enhance sexual potency (or libido) and elevate blood testosterone levels.

12 Claims, 3 Drawing Sheets

COMPOSITION COMPRISING FERTILIZED SHELL EGGS

The present invention relates to the use of fertilized shell eggs to enhance sexual potency (libido), and to compositions comprising such eggs or extracts thereof.

Human sex drive is affected by many factors, such as gender, age, stress levels, and psychological factors. Reduced sex drive affects the general physical and mental well-being of those concerned and is a cause for concern not just for the individual so afflicted but also for his or her sexual partner.

Over the ages many substances have been prepared for enhancing sex drive, but most have not been proven to have any positive effect.

Those treatments with proven success generally fall into two categories—treatment with hormones such as testosterone and treatment with vasodilatory drugs. Vasodilators have a direct physical effect, facilitating erection, rather than affecting the individual's libido or sex drive. On the other hand, with many males low sex drive correlates to low testosterone levels and in these circumstances testosterone administered by injection or transdermally has shown some success. The success however is limited to those whose testosterone level is low—testosterone therapy has not generally been found to be effective in increasing sex drive in the normal adult.

We have now found however that sex drive can be increased by administration into the gastrointestinal tract of fertilized shell eggs, i.e. reptile or avian eggs, or compositions derived therefrom.

As described further below this surprising effect has been proven in double blind clinical trials.

In these trials it has been shown that the subjects having low testosterone levels may have those levels significantly increased. Nonetheless, unlike direct testosterone therapy, the treatment enhances sex drive even in individuals with normal testosterone levels.

Thus viewed from one aspect this invention provides a method of treatment of the human or non-human mammalian body to increase libido or to enhance body testosterone levels, said method comprising administering to said body, preferably into the gastrointestinal tract thereof, e.g. rectally or more preferably orally, a therapeutic agent deriving from fertilized, incubated shell eggs.

By a shell egg is meant an animal egg (e.g. bird or reptile egg) having an opaque shell.

Particularly preferably, the eggs used will be avian eggs, especially those from birds bred for egg production, e.g. hens, geese, ducks, quail, turkeys, ostriches, pheasants, pigeons or the like, most especially hens.

As shown by the trials reported below, the libido enhancing effect occurs with fertilized and incubated eggs rather than with unfertilized and/or unincubated eggs. It is believed that this is as a result of the production of the active factors in the transformation of the egg yolk during embryogenesis.

In the general production of eggs for human consumption, the eggs used are either unfertilized or majoritively unfertilized, and even if fertilized eggs are (inadvertently) presented for human consumption these will generally be unincubated eggs or eggs which have been incubated only for 1 or 2 days.

The eggs used according to the invention are desirably ones in the blastodermal and subsequent preembryonic to protoembryonic stages in which yolk transformation has begun, but the organs of the embryo are barely if at all discernible; this corresponds essentially to the subembryonic liquid stage of embryogenesis (generally 3 to 14 days incubation for a hen's egg), or the period up to the acceleration of calcium uptake by the embryo (this occurs after about 15 days incubation for the hen's egg).

In the case of fertilized hens' eggs used according to the invention, the incubation period is preferably 2 to 15 days especially 3 to 12, particularly 5 to 10, and most preferably about 9 or about 10 days. Eggs incubated for such periods would generally not be considered fit for human consumption due to the degree of transformation of the yolk that has occurred and, for the upper limit due to the presence of an embryo with visible organs.

Viewed from a further aspect the present invention also provides the use of fertilized incubated shell egg for the manufacture of an agent for use in treatment of the human or non-human mammalian body to increase libido.

Viewed from yet a further aspect the present invention provides the use of fertilized incubated shell egg for the manufacture of an agent for use in treatment of the human or non-human mammalian body to enhance testosterone levels therein.

Figure 1:
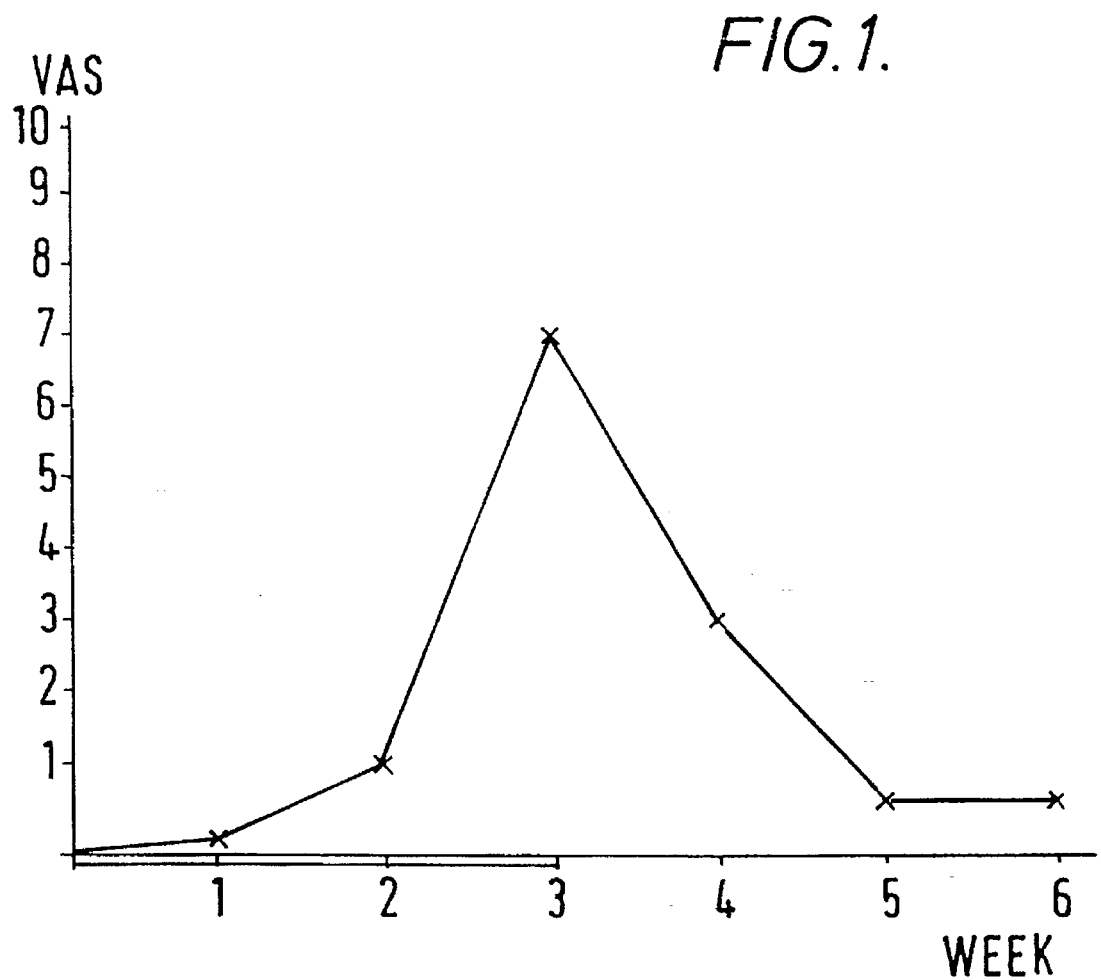
FIG. 1 is a graph illustrating the change over time in the visual analog scale (VAS) score measuring a change is sexual desire for a subject given the composition of the invention.

It is accepted that fertilized eggs, and even fertilized partially incubated eggs, may have been used in the past as a foodstuff since the nutritional value of eggs is well known. Nonetheless the efficacy of fertilized incubated shell eggs as libido or testosterone enhancers has not previously been recognized and in a further aspect of the invention there is provided a novel therapeutic composition comprising a libido and/or testosterone enhancing amount of dried fertilized incubated shell egg or a libido or testosterone enhancing component thereof, optionally together with one or more physiologically tolerable carriers or excipients.

The dried egg may be prepared for example by freeze drying the whole uncooked contents from within the egg shell.

Alternatively however the contents may be divided to remove some or all of the albumin and if desired some or all of the macroscopic structures within and surrounding the yolk (i.e. membranes, blood vessels, embryo etc). Nevertheless for general ease of preparation, either the entire shell content or the yolk fraction of such contents divided physically into yolk and albumin (e.g. by pouring off the albumin) will normally be used to produce the compositions of the invention.

The freeze dried product produced in this way is low in cholesterol and, as long as the eggs' surfaces are sterilized before removal of the contents there should be no health concerns relating to the ingestion of the product. Nonetheless the eggs should derive from a salmonella free flock and thus fertilized hens eggs deriving from Norway, Sweden, Finland, New Zealand and Malta are particularly suitable.

For use in the method of the invention it is of course feasible to administer the egg contents without any extensive preparation, e.g. whisked into a glass of milk. However freeze dried egg has a shelf life which facilitates manufacture, packaging, transport and storage of the compositions according to the invention and by preference such compositions will be administered.

The compositions of the invention are preferably in pulverulent form, optionally including other components serving for example to enhance or mask flavour or to facilitate dispersion of the egg powder in an aqueous fluid for oral administration. The compositions can however contain conventional pharmaceutical carriers or excipients and may be presented in standard administration forms for oral or rectal administration, e.g. powders, tablets, coated tablets, capsules, suppositories, etc. Examples of preferred additives include the vitamins and minerals of conventional daily food supplement compositions, sweeteners such as saccharides, carrotenes, folic acid, citrates, add plant flavourings, and in particular ginseng, vitamin $B_{12}$, vitamin $B_1$ (e.g. thiamine), vitamin C, vitamin E (e.g. $\alpha$-tocopherol), $\beta$-carrotene, folic acid, glucose, fructose, sodium and potassium citrates, magnesium chloride, zinc oxide, and extracts, oils or powders derived from ginseng, aniseed, rosemary, peppermint, hops, camomile, thyme, cloves, and fennel. The egg powder preferably is present at 30 to 90% by weight, particularly 70 to 80% by weight, especially preferably about 75% by weight.

Viewed from a still further aspect, the invention also provides a process for the preparation of a sexual potency or (libido or) testosterone enhancing agent which process comprises incubating fertilized shell eggs into the blastodermal to protoembryonic stage (e.g. for 2–15, preferably about 10 days in the case of hens eggs) and freeze drying the shell contents or a component thereof having a libido or testosterone enhancing activity (e.g. the yolk from which the surrounding albumin has been removed).

The process of the invention in a straightforward embodiment comprises incubating fertilized hens eggs for about 10 days, cracking them open, freeze drying the contents, grinding the resultant product to a powder, and admixing the powder with any desired physiologically tolerable additives such as discussed above.

An embodiment of the process is described in further detail below.

The dosage and treatment duration using the compositions of the invention will depend to some extent on the species and gender of the subject being treated and also on whether the subject has hitherto been experiencing low or reduced sex drive. Where the subject before treatment has low blood testosterone levels, then treatment may need to be carried out for several weeks, e.g. 4 to 20 weeks, before an increase in sex drive is noticed even though an increase in blood testosterone may be detectable earlier. The treatment is intended primarily for humans, either women or more normally men, and in adults with normal sex drive an increase in potency may be manifested after as little as 2 or 3 weeks.

A dosage of 1 to 50 g egg powder, preferably 2 to 20 g per day in one or more (especially two) doses will generally be preferred. Particularly preferably the dosage will be about 5 to 10 g per day in two doses, morning and evening, for a period of 3 to 6 weeks with a 50% reduction in the dosage for subsequent weeks unless low sex drive persists.

Where the powder is prepared from separated yolk, these dosages could be reduced by about 60%.

Higher dosages than the 50 g/day mentioned above may be undesirable for prolonged periods, e.g. over two weeks, as the dosage should not be such as to provoke an allergic reaction.

Figure 2:
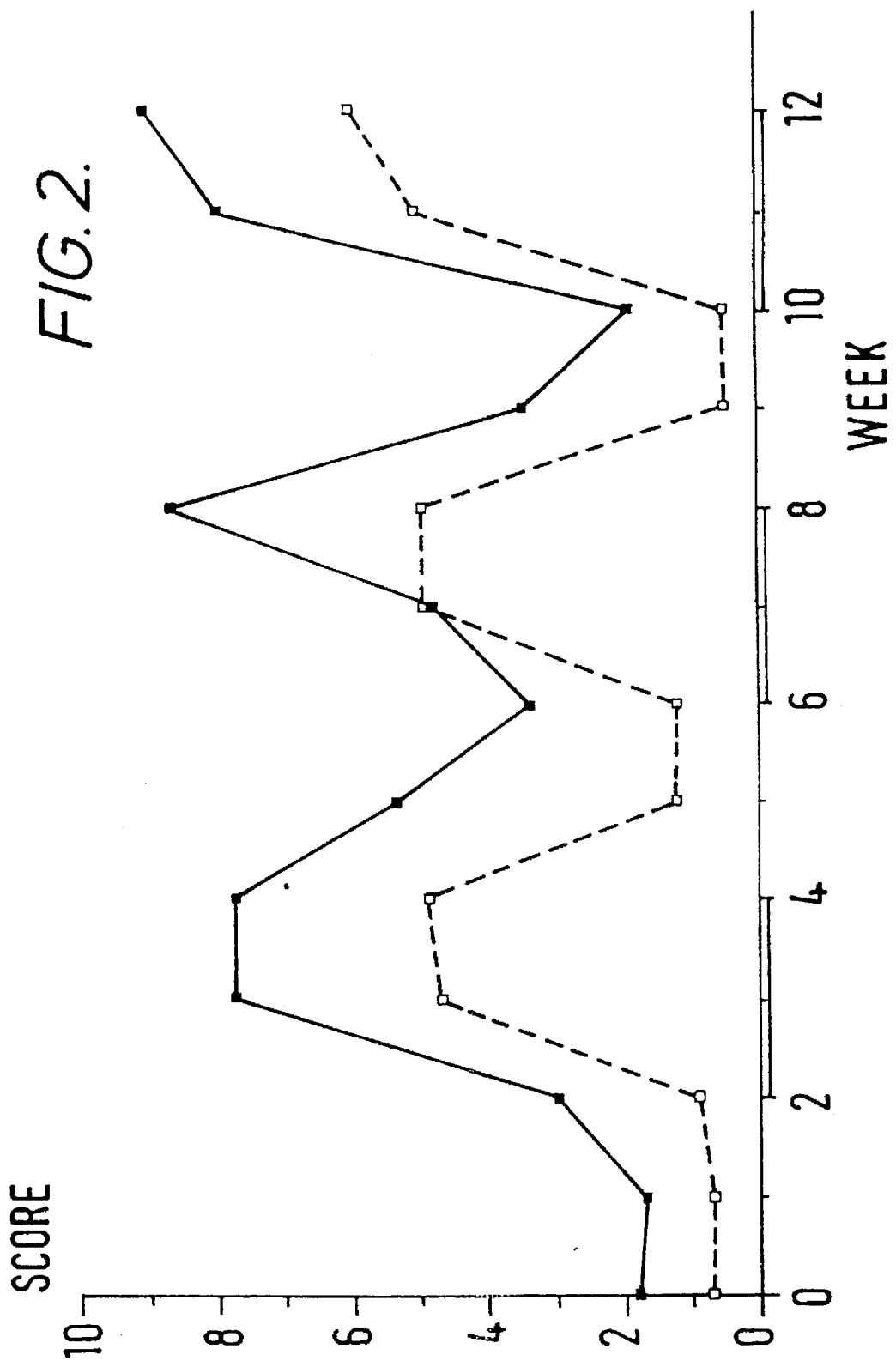
FIG. 2 is a graph illustrating the pattern of change over time in the VAS score for two patients being treated with the composition of the invention.
Figure 3:
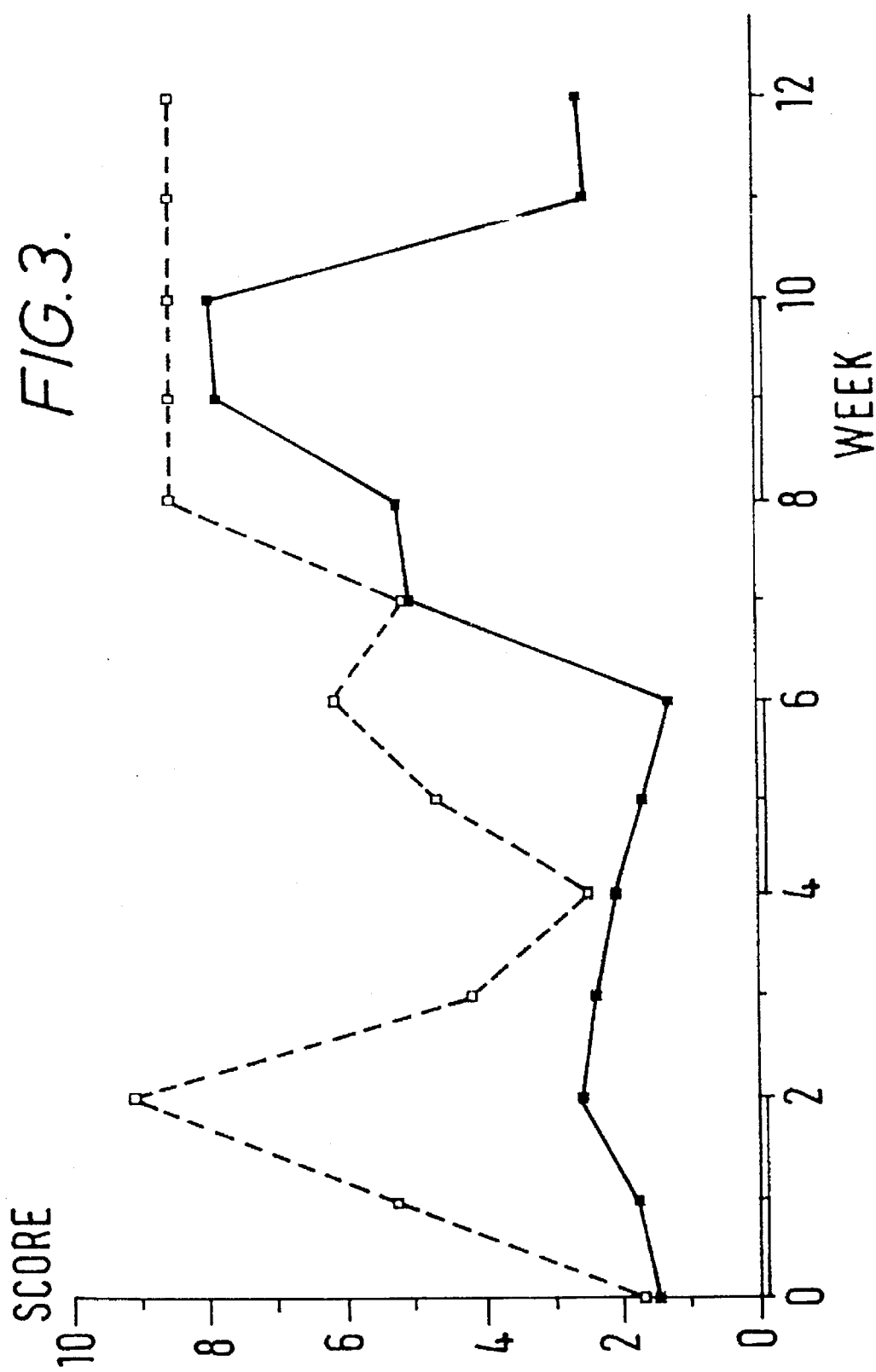
FIG. 3 is a graph illustrating a another pattern of change over time in the VAS score for two patients being treated with the composition of the invention.

Embodiments of the invention will now be described further by reference to the following non-limiting examples, and to the accompanying drawings in which FIGS. 1 to 3 depict graphically patients' responses as VAS scores over trial periods with active agent and placebo. In the Figures, periods of active agent dosage are marked by a doubling of the base line.

EXAMPLE 1

Egg Powder Preparation

Fertilized eggs were collected daily from laying hens, subjected to a surface gassing to sterilize their outer surfaces and placed into storage at 11° C. until a week's batch had been collected. Storage at 11° C. halts embryogenesis and during this period the eggs are rolled to prevent settling out of the contents. The collected week's batch was placed in an incubator maintained at about 39° C. and a relative humidity of about 80%. In the incubator an automatic turner turned the eggs two to three times per day. After five days incubation the eggs are illuminated to determine which were not developing and these were removed. (They can be used for animal feed). After 9 days incubation the eggs were removed, dipped in 70% ethanol, cracked open in a sterile room, and the contents were mixed and placed in a freeze drier. The egg contents were freeze dried to about 2 weight % moisture content over a period of two days at about $-50°$ to $-60°$ C. under vacuum. The crisp, flaky freeze dried product was ground and vacuum packed before further processing as described in Example 2 below.

EXAMPLE 2

Oral Composition

Each foil sealed sachet contains 3.5 g powder having the following composition:

|  | % by weight |
|---|---|
| Dried egg powder (Example 1 above) | 72.10 |
| Glucose | 1.40 |
| Fructose | 0.70 |
| Potassium citrate | 1.10 |
| Sodium citrate | 1.40 |
| Magnesium chloride | 0.70 |
| Zinc oxide | 1.10 |
| β-carrotene | 0.70 |
| Ascorbic acid | 5.50 |
| α-tocopherol (premix*-0.01% active) | 6.10 |
| Vitamin $B_{12}$ (premix*-5% active) | 2.10 |
| Folic acid (premix*-0.5% active) | 0.70 |
| Thiamine chloride (premix*-25% active) | 0.30 |
| Plant extracts: | |
| Ginseng | 1.80 |
| Aniseed | 1.60 |
| Rosemary | 0.70 |
| Peppermint | 0.40 |
| Hop | 0.20 |
| Camomile | 0.30 |
| Thyme | 0.30 |
| Clove | 0.30 |
| Fennel | 0.50 |

\* — premix manufactured from textured maize starch.

For administration, the contents of one sachet is mixed into water or a drink such as milk or orange juice, and swallowed. For normal treatment one sachet is taken morning and evening.

EXAMPLE 3

First Trial

To document the effect of the egg powder on sexual desire, a pilot study was carried out. Open studies have obvious weaknesses (bias, the effect of placebos, etc.).

Accordingly, in order to validate the indications of an effect which were reported during the pilot studies, it was decided to carry out a controlled double-blind study. The objective of this study was to examine and compare to see whether the powder has any more effect on sexual desire than a placebo in a group of men. The study was arranged so as to be a randomized, placebo-controlled, double-blind study lasting over a period of six weeks. This means three weeks with the active preparation and three weeks with a placebo.

Sixteen men without reported sexual dysfunction and whose ages ranged from 47 to 60, the average age being 52.5 years, took part in the study. The average weight was 84 kg and the average height 181 cm. This gives a "Body Mass Index" (BMI) of 25.6 kg/m$^2$, i.e. the persons were of normal weight.

None of the participants used medication regularly. Half of the participants were given the preparation according to the invention for the first three weeks, while the remaining eight were given a placebo. In the second three weeks, the situation was reversed.

The study was carried out as a cross-over study without a wash-out period between the two periods of treatment. This method was chosen because the number of persons in the test was smaller than in a parallel group method.

Dried egg powder from 9 day incubation eggs prepared as in Example 1 was measured out into sachets of 3 g having the same relative composition as the material of Example 2, i.e. 72.1% egg powder, one sachet to be taken in the morning and one in the evening. The contents of the sachet were stirred into a glass of juice or water and drunk immediately. Each participant was given a box containing 50 sachets corresponding to three week's treatment together with an equivalent amount of the placebo. Unused sachets were returned in order to confirm compliance.

The placebo used was identical to the preparation according to the invention other than that the egg powder therein derived from fresh, non-incubated, fertilized eggs.

Further, the study was based on the participants' own evaluation of their sexual desire, judged by means of a 10 cm long visual analog scale, VAS.

The participants made weekly evaluations of the changes in their sexual desire, both in the active period and in the placebo period. At the end of each period of treatment, an evaluation was also made of whether it was desirable to continue in the treatment.

The participants were instructed in the use of visual analog scales and it was also made possible to give a response as to whether any side effects were registered as a consequence of the treatment.

The participants were also instructed to report any discomfort.

In Table 1 below the average score is shown of all the participants who were given the preparation according to the invention in the first period and the placebo in the second:

TABLE 1

| Average score (N = 8) Preparation according to invention → placebo | | | | | | |
|---|---|---|---|---|---|---|
| Week No. | 1 | 2 | 3 | 4 | 5 | 6 |
| Score (cm) | 0.11 | 1.69 | 7.84 | 2.48 | 0.18 | 0.18 |

As can be seen from the Table, there was an increase in the VAS value from week two, and high values in weeks three and four.

In Table 2 below the average score is shown for the second group, viz the group which was given the placebo in the first period and the preparation according to the invention in the second period:

TABLE 2

| Average score (N = 8) Placebo → preparation according to invention | | | | | | |
|---|---|---|---|---|---|---|
| Week No. | 1 | 2 | 3 | 4 | 5 | 6 |
| Score (cm) | 0 | 0.13 | 0.13 | 0.31 | 1.74 | 7.75 |

As can be seen from the Table, the values are modest in the placebo period and there is a significant increase in the period when the preparation according to the invention was tested.

Table 3 shows the average score for all the participants, by the week for the two periods:

TABLE 3

| Average score for all participants (N = 16) | | | |
|---|---|---|---|
| | Mean Score | | |
| | Week 1 | Week 2 | Week 3 |
| Period with preparation according to invention | 0.21 | 1.72 | 7.80 |
| Placebo period | 1.24 | 0.16 | 0.25 |

As can be seen from this Table, the preparation according to the invention gives a significantly higher value than the placebo in weeks two and three. The relatively high value for the placebo in week one is presumed to be due to a carry-over effect experienced by the participants who received the preparation according to the invention before changing over to the placebo. This is also made apparent in Table 1. Some of the effect of the preparation according to the invention is carried over into the first week of the placebo period since, as mentioned hereinabove, no wash-out period was used between the observation periods.

FIG. 1 of the accompanying drawings displays graphically the change over time of the VAS score for one participant who was given the preparation according to the invention in the first period and the placebo in the second.

The preparation according to the invention thus seems, according to these results, to take effect after two to three weeks treatment.

None of the participants in this study reported any discomfort or side effects in connection with the treatment.

The conclusion drawn from this first trial was that the preparation according to the invention really does have an effect on sexual desire and therefore, meets a long felt need, especially for those groups of vulnerable persons whose sexual desire is reduced to a greater or lesser extent owing to natural or therapeutic reasons.

EXAMPLE 4

Second Trial

A second trial was subsequently carried out under more stringent conditions using the product of Example 2 as the test material and using as the placebo a product identical thereto other than in the replacement of the egg powder by 72.10% of a powder deriving from baked wheat rolls and corn flakes. The additional ingredients dominated the overall taste of the compositions making discrimination between active product and placebo by taste non-feasible.

For the second trial 31 men, aged between 38 and 65 years (average 50.9), and admitting to reduced sexual desire were selected. The patients had a clinical examination and blood testosterone was measured. For patients whose initial blood testosterone values were low, blood testosterone was measured at the end of treatment. For these patients (total 11) an average increase of 25% in blood testosterone was found.

The dosage used was 7 g/day of the composition of Example 2 (or the placebo) administered orally morning and evening.

The trial was a multiple cross over double-blind with patients receiving placebo or active composition for a total of twelve weeks for alternating two week periods.

Certain patients demonstrated a clear saw-tooth pattern as demonstrated for patients 17 (open squares) and 20 (filled squares) in FIG. 2 of the accompanying drawings. For others, an initial strong response led to subsequent stabilization of libido at a high plateau level (see patient 1 (open squares) in FIG. 3 of the accompanying drawings). Other patients, especially those with low initial testosterone levels took more time to show a response in terms of increased sex drive. For such patients it is considered that the active agent would have to be administered for a more prolonged period.

Overall, for this group of sexually dysfunctional men, a positive response in terms of increased libido was noted by 58% over the test period.

We claim:

1. A composition comprising a libido or testosterone enhancing mount of dried uncooked fertilized incubated avian egg wherein said fertilized egg is incubated to the blastodermal to protoembryonic stage, optionally together with one or more physiologically tolerable carriers or excipients.

2. A composition as claimed in claim 1 wherein said fertilized incubated avian egg is freeze dried.

3. A composition as claimed in claim 2 wherein said avian egg is hens egg.

4. A composition as claimed in claim 1 comprising freeze dried arian egg yolk.

5. A composition as claimed in claim 3 wherein said dried egg is dried hens egg incubated for about 10 days.

6. A composition as claimed in claim 1 in unitary dosage form containing from about 70 to about 80% by weight dried egg.

7. A method of treatment of the human body to increase libido or to enhance body testosterone levels, said method comprising administering to said body a composition of claim 1.

8. The method as claimed in claim 7 wherein said agent is administered orally.

9. The method as claimed in claim 7 wherein the amount of the agent administered comprises from about 1 to about 50 g on a dry solids basis daily.

10. The method as claimed in claim 9 wherein said agent is administered in dried pulverulent form.

11. A process for the preparation of a sexual potency or libido or testosterone enhancing agent which process comprises incubating fertilized avian eggs into the blastodermal to protoembryonic stage and freeze drying the uncooked shell contents of the eggs, or the yolk thereof to produce said agent in dried form.

12. A process as claimed in claim 11 comprising incubating fertilized hens eggs for about 10 days, freeze drying the uncooked contents of the eggs, grinding the resultant product to a powder, and admixing the powder with any desired physiologically tolerable additives.

* * * * *